(12) United States Patent
Painter et al.

(10) Patent No.: US 7,427,412 B1
(45) Date of Patent: Sep. 23, 2008

(54) GEL-BASED COSMETIC COMPOSITION

(75) Inventors: Rachel J. Painter, Brooklyn, NY (US); Isaac David Cohen, Brooklyn, NY (US)

(73) Assignee: Color Access, Inc., Melville, NY (US)

( * ) Notice: Subject to any disclaimer, the term of this patent is extended or adjusted under 35 U.S.C. 154(b) by 1054 days.

(21) Appl. No.: 09/622,510

(22) PCT Filed: Jun. 21, 2000

(86) PCT No.: PCT/US00/17098

§ 371 (c)(1),
(2), (4) Date: Oct. 19, 2000

(87) PCT Pub. No.: WO01/00154

PCT Pub. Date: Jan. 4, 2001

(51) Int. Cl.
*A61F 13/00* (2006.01)
*A61K 9/70* (2006.01)
*A61K 31/175* (2006.01)
*A61K 31/695* (2006.01)

(52) U.S. Cl. ............... 424/443; 424/447; 514/57; 514/58; 514/63

(58) Field of Classification Search ............ 424/401, 424/443, 447; 514/57, 58, 63
See application file for complete search history.

(56) References Cited

U.S. PATENT DOCUMENTS

| | | | |
|---|---|---|---|
| 3,896,807 A * | 7/1975 | Buchalter | 604/289 |
| 4,706,693 A | 11/1987 | Spector | 132/79 R |
| 4,776,356 A * | 10/1988 | Jou et al. | 15/244.4 |
| 4,927,283 A | 5/1990 | Fitjer | 401/132 |
| 5,137,040 A * | 8/1992 | Iosilevich et al. | 132/320 |
| 5,401,113 A | 3/1995 | Gueret | 401/208 |
| 5,562,642 A * | 10/1996 | Smith et al. | 604/289 |
| 5,599,549 A * | 2/1997 | Wivell et al. | 424/401 |
| 5,861,165 A | 1/1999 | Joulia | 424/401 |
| 6,001,373 A * | 12/1999 | Igo-Kememes et al. | 424/401 |
| 6,488,945 B2 * | 12/2002 | Sato | 424/401 |

FOREIGN PATENT DOCUMENTS

| | | |
|---|---|---|
| CA | 2 276 029 | 5/1999 |
| CN | 1073111 | 6/1993 |
| DE | 3615358 | 12/1987 |
| EP | 823 228 | 2/1998 |
| FR | 2455902 | 12/1980 |
| FR | 2628394 | 9/1989 |
| JP | 03006283 | 1/1991 |
| JP | 08-325119 | 12/1996 |
| WO | WO 95/09598 | 4/1995 |
| WO | WO 98/15262 | 4/1998 |

* cited by examiner

*Primary Examiner*—Johann Richter
*Assistant Examiner*—Konata M George
(74) *Attorney, Agent, or Firm*—Cynthia R. Miller; Karen A. Lowney

(57) ABSTRACT

The invention relates to cosmetic compositions comprising an elastic, non-rigid, porous support in which a low-viscosity, gellant-containing, single phase otherwise unstable cosmetic formulation has been incorporated, and a method of making same.

15 Claims, No Drawings

GEL-BASED COSMETIC COMPOSITION

FIELD OF THE INVENTION

The invention relates to the field of cosmetics. More specifically, the invention relates to gel-based color cosmetics.

BACKGROUND OF THE INVENTION

A majority of color cosmetics are formulated with one or more inorganic pigment particles which confer the desired color to the composition. These particles are normally iron oxides, or titanium dioxide, having particle sizes ranging from about 0.5-200 nm. Obviously, these pigments are an essential part of color cosmetics, and yet the very nature of these particles makes it difficult to formulate a product around them. These particles are soluble in neither oil nor water, and therefore must simply be suspended in the oil or water vehicle making up the base of the product. To achieve this, particularly in a single phase product, it is usually necessary to incorporate one or more thickeners or suspending agents into the formula. Without these suspending agents, which are usually waxes, it is virtually impossible to make a stable single phase formulation, as all the pigment particles soon settle out. Unfortunately, the suspending agents, in performing their required function, make the formula thicker and heavier than might otherwise be desirable. The texture of such formulas may be unacceptable to some consumers, particularly in warmer weather, when the lightest possible makeup is desired. Also, the suspending agents can interfere with the purity of color achieved in the formula. Thus, to date it has proven difficult, if not impossible, to provide a stable color cosmetic that is substantially nothing more than a pure color suspension, without the addition of suspending agents. The present invention now provides a unique solution to this formulation problem.

SUMMARY OF THE INVENTION

The invention relates to a cosmetic or pharmaceutical composition comprising an elastic, non-rigid, porous support in which a low-viscosity, gellant-containing, otherwise unstable cosmetic or pharmaceutical formulation is integrated. The support acts as a stabilizer for the formulation, thereby permitting the preparation of low-viscosity formulas, reducing or completely eliminating the need for thickeners or suspending agents to keep any included inorganic pigments from settling out. The invention also relates to a method of making a stable cosmetic composition comprising preparing a low-viscosity, gellant-containing, otherwise unstable cosmetic formulation, and incorporating the formulation into a porous, non-rigid support. Preferably, the method includes the steps of preparing the formulation under conditions which do not permit gelling, adding the ungelled formulation to a non-rigid porous support, and allowing the formulation to gel within the support. The formulation in the support is nearly water-thin and very lightweight, and is accessed by pressing on the surface of the support, with either the fingers or another applicator.

DETAILED DESCRIPTION OF THE INVENTION

The use of sponges or other porous devices to apply cosmetics to the skin is of course well-known (e.g., EP 823228; U.S. Pat. No. 5,401,113; CN 1073111; FR 2628394; U.S. Pat. No. 4,927,283; DE 3615358; U.S. Pat. No. 4,706,693) Unlike many other porous-type applicators, the present combination does not have a separate reservoir of the formulation to be applied, from which the formulation is ultimately drawn to supply the porous applicator; instead, the entire formulation is distributed integrally throughout the support, the combination of support and formulation itself acting as the sole reservoir and source of product to be applied. The present invention also differs from such cosmetic uses of sponges in that the sponge in the present case is used essentially as a stabilizer for a very low viscosity cosmetic composition, which composition would be otherwise be unstable. By "otherwise unstable", as used in the present specification and claims, is meant a formulation that, because of its low viscosity, is unable to stably maintain a suspension of inorganic pigment; in other words, contained pigment particles would quickly settle out of the formulation upon resting.

Although the formulation is gel-based, it contains relatively low levels of gellant, so that the gelled formulation, in the absence of the support, is inadequate to support the heavy pigments. Too much gellant in the formulation will result in a hardening of the porous support, and no payoff of the formulation when the support is compressed. In other words, the gellant should be used at a level which would be inadequate to stably support the presence of pigment particles in the formulation. Although levels are low, the presence of the gellant is essential, however, to permit the formulation to set up within the sponge; otherwise, the formulation will simply drip out of the support. The amount of gellant to be used, in functional terms, is that amount that will produce a fluid consistency below that of a paste; preferably, the formulation is nearly water-thin. The amount used will of course vary in absolute terms depending upon the identity of the gellant used, but is readily determinable for any gellant of interest.

The identity of the gellant will depend on the identity of the phase to be gelled. If the gelled phase is an oil phase, the gellant can be selected from any oil-soluble gellants, such as dextrin fatty acid esters, such as dextrin palmitate; cholesterol and derivatives, such as lanosterol, silicone gellants, such as organopolysiloxane elastomers; oil soluble cellulose derivatives, such as ethyl cellulose, and polymers or mixed copolymers, such as ethylene/methacrylic acid copolymer, ethylene/acrylic acid copolymer, or polyethylene. The oil base may be any cosmetically acceptable oil, either volatile or non-volatile, or a mixture of both. For example, suitable volatile oils include, but are not limited to, both cyclic and linear silicones, such as cyclomethicone; or straight or branched chain hydrocarbons having from 8-20 carbon atoms, such as decane, dodecane, tridecane, tetradecane, and C8-20 isoparaffins.

Non-volatile oils include, but are not limited to, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and non-volatile hydrocarbons, such as isoparaffins, squalane, or petrolatum.

The gelled phase may also be aqueous. In the case in which the base is aqueous, the gellant will be a water-soluble gellant, such as carbomer, hydroxypropyl methylcellulose, hydroxyethylcellulose, hydroxy propyl guar, hydroxypropyl cellulose, potato starch modified, or acrylates/C10-C30 alkyl acrylates crosspolymer. Although the advantage of the invention is particularly great for use with a single phase composition, it is also possible to employ the porous support concept with a low viscosity emulsion, either oil-in-water or water-in-oil, utilizing the appropriated gellant to gel the emulsion's external phase.

The amount of base in the formulation, whether single phase oil or water, or a water-and-oil emulsion, will be in the range of from about 30 to about 99.6% by weight of the formulation. In one preferred embodiment, the base is an anhydrous oil base, and more preferably, a silicone base, and the gellant is a cholesterol derivative, such as lanosterol. When using a cholesterol derivative, the amount of gellant employed ranges from about 0.1 to about 10%, preferably about 0.1 to about 2%, by weight of the formulation.

The formulation may also contain additional components. Particularly in the case of a color cosmetic product, the formulation will contain one or more pigments, which may be organic, inorganic, or a combination thereof. Examples of useful pigments include, but are not limited, inorganic pigments such as iron oxides (yellow, red, brown or black), ferric ammonium ferrocyanide (blue), manganese violet, ultramarine blue, chrome oxide (green), talc, lecithin modified talc, zeolite, kaolin, lecithin modified kaolin, titanium dioxide (white) and mixtures thereof. Other useful pigments are pearlants such as mica, bismuth oxychloride and treated micas, such as titanated micas and lecithin modified micas.

Useful organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C lakes and blends thereof. Also included are polymer pigments, e.g., nylon powder, polyethylene, and polyesters. The polyesters can include linear, thermoplastic, crystalline or amorphous materials produced using one or more diols and one or more dicarboxylic acids copolymerized with colorants. Other pigments to be used in the invention will be apparent to one of ordinary skill in the art.

The formulation can also be a non-makeup product, i.e., a skincare product without added pigment. In this regard, the formulation may also contain one or more active ingredients, such as sunscreens, self-tanning agents, chemical exfoliators, such as AHAs or BHAs, antioxidants, anti-irritants, anti-inflammatories, vitamins, skin-whiteners, and the like. Additional components, such as skin conditioners, emollients, fillers, powders, pigment wetting agents, and other such materials as are consistent with the intended use of the final product. The formulation is characterized further, however, in containing less than about 5%, preferably less than about 1.0%, by weight of waxes or suspending agents. This is in contrast to normal low-viscosity compositions, which would usually require about 10% of suspending agents in order to keep suspended particles from settling out.

The formulation after preparation is added, in a pourable state, to the porous, non-rigid support. As the amount of gellant used is low, even a fully gelled formulation may be pourable into the support. However, it is preferred that the formulation be maintained in a non-gelled state until it is in the sponge, so that the gel actually sets up within the support. Frequently, as will be the case with an anhydrous oil base, the formulation will be a hot pour, in which the formulation is added while at elevated temperature to the support and allowed to cool, and gel, after it has penetrated the support.

The support can be virtually any porous material that is cosmetically acceptable, and compatible with the cosmetic formulation to be added to it. The support will ordinarily be a foam or a sponge, such as a natural sponge, a foamed rubber such as natural rubber, synthetic polyisoprene, nitrile, neoprene, ethylene propylene diene type M, or polyurethane, or a foamed polyethylene. Pore size should be in the range of from about 300-100 pores per inch. Care should be taken to ensure that the pore size is no smaller than the size of any particles, such as pigments or powders, found in the formulation, so as to avoid clogging of the pores by the particles.

The preparation of the final product is straightforward: after preparation of the formulation, the liquid formulation is poured into the support, or alternately, the support is dipped or immersed in the formulation. In the case of a formulation that has not been gelled prior to addition to the support, the composition comprising support and formulation is left at room temperature for a time sufficient for the gellant to set up the formulation within the support. This time will vary depending upon the set point of any given gellant, but will ordinarily be no longer than about 15 minutes within the support. The composition is then ready to use. Although the level of gellant is selected so as to produce an inherently unstable formulation, the formulation is sufficiently gelled within the support to prevent its running out of the support in an uncompressed state; however, because the level is so low, when pressure is applied to the support, whether by pressinq of the fingers or the skin surface to which it will be applied, or by pressing of another applicator onto the support, the gel readily breaks, releasing a lightweight, non-pasty, non-waxy, substantially water-thin product which is easily applied to the skin. This delivery system also exhibits a unique, silky, luxurious feel to the touch.

The formulation of the invention in a preferred embodiment will be a color cosmetic, such as a blush, foundation, eyeshadow, mascara (hair or lash), lip gloss, and the like. However, it can also be a skin care product, such as sunscreen, self-tanner, moisturizer, anti-acne product, anti-wrinkle composition, and the like, or it can be a pharmaceutical product intended for topical application to the skin, for example, an antibiotic, a wound-healing agent, an anti-inflammatory, and the like.

For practical use, the invention will normally be placed in a cosmetic-type package, for example, a compact or jar, for ease of handling, and to prevent drying out. However, it may also be used as an applicator itself, e.g. alone or on a stick-type device. The invention therefore also provides a unit package comprising the cosmetic composition described herein. The invention will be further elucidated by reference to the following non-limiting example.

EXAMPLES

Example 1

A Formulation of the Invention is Prepared as Follows

| Material | Weight % |
| --- | --- |
| red iron oxide | 1.00 |
| yellow iron oxide | 2.00 |
| black iron oxide | 0.20 |
| titanium dioxide | 17.20 |

-continued

| Material | Weight % |
| --- | --- |
| polyglyceryl-3 diisostearate | 0.50 |
| phenyltrimethicone | 64.20 |
| polymethyl methacrylate | 7.00 |
| lauroyl lysine | 3.50 |
| dimethicone/cyclomethicone | 4.00 |
| lanosterol | 0.40 |

The composition is prepared as follows:
1. Pigments are mixed under a propeller in polyglyceryl-3 diisostearate and 20% phenyl trimethicone.
2. The pigment mixture is then run through a roller mill three times until the pigments are thoroughly wet out.
3. All the materials but the lanosterol are mixed together until homogeneous.
4. The mixture is heated to 100-105° C.
5. Lanosterol is slowly added under mixing.
6. Mixing is continued for about 10 minutes or until all lanosterol goes into solution.
7. If the formulation is to be used hot, a sponge (e.g., Qosmedix non-latex hydrophilic open cell sponge, 200 pores per inch) is immersed into the hot mixture until it is fully saturated, ordinarily about 5 minutes. Excess material is wiped off and the sponge is inserted into a compact.
8. If the formulation is to be applied at room temperature, the sponge is immersed into the mixture as described in paragraph 7. above, while the mixture is being agitated in order to preserve homogeneity while absorption is occurring.

We claim:

1. A cosmetic or pharmaceutical composition comprising a non-rigid, porous support in which a low-viscosity, gellant-containing, otherwise unstable cosmetic or pharmaceutical formulation is incorporated, which composition comprises an oil phase, in which the gellant is selected from the group consisting of cholesterol and derivatives thereof, dextrin fatty acid esters, silicone gellants, oil-soluble cellulose derivatives, and oil-soluble polymers, and in which the porous support has a pore size of from about 100 to about 300 pores per inch.

2. A cosmetic or pharmaceutical composition according to claim 1 in which the gellant is a cholesterol derivative.

3. The composition of claim 2 in which the gellant is lanosterol.

4. A cosmetic or pharmaceutical composition according to claim 1 in which the oil phase comprises a silicone oil.

5. The composition of claim 4 in which the formulation is a water-and-oil emulsion.

6. The composition of claim 4 which is anhydrous.

7. A cosmetic or pharmaceutical composition according to claim 1 in which the porous support is made of a material selected from the group consisting of a natural sponge, a foamed rubber or a foamed polyethylene.

8. A cosmetic or pharmaceutical composition according to claim 1 which composition also contains at least one pigment.

9. The composition of claim 8 which comprises an inorganic pigment.

10. A cosmetic or pharmaceutical composition according to claim 1 which composition contains substantially no waxes or suspending agents.

11. A cosmetic or pharmaceutical composition made by (a) preparing a low viscosity, gellant-containing, otherwise unstable formulation; and (b) incorporating the formulation into a porous, elastic, non-rigid support, in which the formulation is permitted to gel within the support, in which formulation comprises an oil, and the gellant is selected from the group consisting of cholesterol derivatives, dextrin fatty acid esters, silicone gellants, and oil-soluble polymers.

12. The composition of claim 11 in which the oil comprises a silicone oil.

13. The composition of claim 11 in which the gellant is a cholesterol derivative.

14. The composition of claim 11 in which the gellant is lanosterol.

15. A cosmetic composition comprising an elastic, non-rigid porous support into which a low-viscosity, cholesterol or cholesterol derivative gellant-containing, otherwise unstable formulation has been integrated, the formulation also comprising at least one inorganic pigment, and an anhydrous base, in which the gellant is lanosterol.

* * * * *